(12) United States Patent
Hongo et al.

(10) Patent No.: US 7,984,739 B2
(45) Date of Patent: Jul. 26, 2011

(54) HEATER UNIT AND THERMAL FUSION APPARATUS FOR SYNTHETIC RESIN MEMBERS AND THERMAL FUSION METHOD FOR SYNTHETIC RESIN MEMBERS

(75) Inventors: Susumu Hongo, Hiroshima (JP);
Takafumi Kiyono, Hiroshima (JP);
Youzou Katsura, Hiroshima (JP);
Yasuhiro Mitsumoto, Hiroshima (JP);
Shingo Henmi, Hiroshima (JP)

(73) Assignee: JMS Co., Ltd., Hiroshima-shi (JP)

( * ) Notice: Subject to any disclaimer, the term of this patent is extended or adjusted under 35 U.S.C. 154(b) by 906 days.

(21) Appl. No.: 11/658,430

(22) PCT Filed: Jul. 26, 2005

(86) PCT No.: PCT/JP2005/013641
§ 371 (c)(1),
(2), (4) Date: Apr. 12, 2007

(87) PCT Pub. No.: WO2006/011475
PCT Pub. Date: Feb. 2, 2006

(65) Prior Publication Data
US 2009/0038756 A1    Feb. 12, 2009

(30) Foreign Application Priority Data

Jul. 26, 2004 (JP) .................................. 2004-217933
Jul. 26, 2004 (JP) .................................. 2004-217936

(51) Int. Cl.
*B29C 65/32* (2006.01)

(52) U.S. Cl. ........ 156/362; 156/423; 156/498; 156/581; 156/583.1

(58) Field of Classification Search .................. 156/350, 156/358, 362, 379.6, 379.8, 423, 498, 499, 156/567, 581, 583.1; 604/174, 177; 219/633, 219/634; 29/777, 785
See application file for complete search history.

(56) References Cited

U.S. PATENT DOCUMENTS

| | | | | |
|---|---|---|---|---|
| 4,246,461 A | * | 1/1981 | Jeppson | 219/633 |
| 4,386,255 A | * | 5/1983 | Berkman et al. | 219/634 |
| 4,478,667 A | * | 10/1984 | Fitko | 156/307.3 |
| 4,790,901 A | * | 12/1988 | Kettelhoit et al. | 156/498 |
| 4,921,569 A | * | 5/1990 | Held | 156/380.6 |
| 5,439,720 A | | 8/1995 | Choudhury | |

FOREIGN PATENT DOCUMENTS
JP         53-128166          11/1978
(Continued)

OTHER PUBLICATIONS

Machine Translation of JP 07-156272. Date Unknown.*

*Primary Examiner* — Michael A Tolin
(74) *Attorney, Agent, or Firm* — Westerman, Hattori, Daniels & Adrian, LLP

(57) ABSTRACT

It is intended to provide a method of producing thermally fused synthetic resin members for medical use which makes it possible that, in the case of thermally fusing synthetic resin members for medical use, for example, a relatively soft thermoplastic tube constituting an AVF needle with another part being harder than the tube such as a needle base (hub) of a wing needle, or a part provided with a fitting connector being harder than the tube (for example, a blood circuit, an extension tube, an infusion set or the like), the connecting parts of the thermoplastic tube member and the other member harder than the thermoplastic tube member can be quickly and uniformly thermal-fused and the production process can be automatically and continuously performed while keeping a high productivity; and a production apparatus therefor.

6 Claims, 3 Drawing Sheets

FOREIGN PATENT DOCUMENTS

| | | |
|---|---|---|
| JP | 53-128167 | 11/1978 |
| JP | 01-097473 | 4/1989 |
| JP | 02-185426 | 7/1990 |
| JP | 07-156272 * | 6/1995 |
| JP | 09-290461 | 11/1997 |
| JP | 2004-167884 | 6/2004 |

* cited by examiner

US 7,984,739 B2

HEATER UNIT AND THERMAL FUSION APPARATUS FOR SYNTHETIC RESIN MEMBERS AND THERMAL FUSION METHOD FOR SYNTHETIC RESIN MEMBERS

TECHNICAL FIELD

The present invention relates to: a heater unit for use in thermal fusion of synthetic resin members for medical use (hereinafter referred to as a heater unit); a thermal fusion apparatus for synthetic resin members for medical use configured to have the aforementioned heater unit (hereinafter referred to as a thermal fusion apparatus); and a thermal fusion method of synthetic resin members for medical use using the aforementioned thermal fusion apparatus; particularly to a heater unit for mounting a medical tube made of thermoplastic resin being connected with a thermoplastic resin member for medical use which is harder than the aforementioned tube, by inserting the thermoplastic resin member into the tube so that both are fitted to each other; a thermal fusion apparatus for synthetic resin members for medical use comprising the aforementioned heater unit; and a thermal fusion method of thermoplastic resin members for medical use using the aforementioned thermal fusion apparatus.

The present invention is suitable as production facilities for AVF needles, winged intravenous needles and the like, and for production methods of AVF needles, intravenous needles and the like.

BACKGROUND ART

Traditionally, for connecting relatively soft synthetic resin tube, for example, a soft vinyl chloride tube of an AVF needle, with a hard tubular connector for medical use such as of polycarbonate or a needle base (hub), there is a method of bonding with a solvent or adhesive, or a method called blocking in which the aforementioned connector or needle base (hub) is inserted into the aforementioned soft vinyl chloride tube and the whole assembly is subjected to a heating environment to connect the two together. An example of the problem which arises when adopting the aforementioned method of bonding with a solvent and adhesive include degradation, embrittlement, and solvent cracking of the material due to the solvent. Also, in the blocking method, there is a problem that heating the entire assembly will cause the heat shrinkage of the entire body thereby leading to unstable product dimensions after blocking, and further there is a risk that keeping the assembly in a heating environment for long hours will cause the stabilizer etc. contained in the resin constituting respective parts to bleed out thus leading to degradation and color change of the material.

Further, as a method of connecting thermoplastic members, there is proposed in the patent documents 1, 2, and 3 a method of connecting thermoplastic tube members, in which an electrically terminated annular conductor is interposed between the inner surface of a large-diameter thermoplastic tube member and the outer surface of a small-diameter thermoplastic tube member, the tip of a small-diameter tube member being inserted into and connected to the large-diameter tube member, and the aforementioned conductor is caused to generate Joule heat uniformly in its circumferential direction through high frequency induction heating from outside the large-diameter tube member thereby melting and fusing the constituent material of the tube members in the region where the conductor is interposed.

Patent document 1: JP, A, 09-290461
Patent document 2: JP, A, 53-128166
Patent document 3: JP, A, 53-128167

DISCLOSURE OF THE INVENTION

Problems to be solved by the Invention

In the case of connecting synthetic resin members for medical use, for example, fabricating an AVF needle, when connecting by thermal fusion the thermoplastic tube member constituting the AVF needle and other part which is harder than the aforementioned tube such as a needle base (hub) of a winged needle or a connector for the connection of a blood circuit, an extension tube, an infusion set, or the like, it is necessary to have the connection portion of the aforementioned thermoplastic resin members to be thermally fused to be clamped by a melting die with the former being fitted into the latter so as to be heated and fused rapidly and uniformly. However, it was difficult to perform thermal fusion satisfying the aforementioned requirement by means of a known thermal fusion apparatus for synthetic resin members as described above. In particular, it was difficult to perform rapidly and automatically in a continuous process the step of mounting the synthetic resin members for medical use onto the thermal fusion apparatus, the step of thermally fusing the aforementioned synthetic resin members, the step of cooling the connection part after the aforementioned thermal fusion, and the like.

Means for Solving the Problem

The present invention has solved the aforementioned problems by providing: a heater unit characterized by comprising a heat provider which can mount synthetic resin members for medical use to be thermally fused in a connected state and thermally fuse the connection part of the synthetic resin members thus mounted, and heat conductive plates disposed vertically above and below the aforementioned heat provider, wherein the aforementioned heat conductive plates can be heated so as to be able to transfer necessary amount of heat to thermally fuse the aforementioned synthetic resin members for medical use; a thermal fusion apparatus configured to have the aforementioned heater unit; a thermal fusion method of synthetic resin members for medical use utilizing the aforementioned thermal fusion apparatus; and thermally fused articles of synthetic resin members for medical use produced by the aforementioned thermal fusion method.

Since the heater unit of the present invention is configured such that the substantial amount of heat needed for the heat provider to thermally fuse the synthetic resin members for medical use is not provided by the heat generation of the heat provider itself, but instead the heat conductive plates constituting the aforementioned heater unit are heated and then each part of the heat provider is uniformly heated by conduction heating from the aforementioned heated heat conductive plates, the aforementioned heat provider can thermally fuse the synthetic resin members for medical use uniformly. In contrast, in the case in which heating is performed by making the heat provider, for example, the melting die itself generate heat, for example heating of the melting die is performed by making the melting die generate Joule heat by high frequency induction heating, the amount of heat to be generated will vary depending on the shape of the melting die and the respective portions of the die, and therefore the generation of Joule heat will become stronger or weaker depending on the respective portions of the die, thus causing a problem that obtaining uniform connection of the thermal fusion part will become difficult when thermally fusing the synthetic resin members using the aforementioned dies. However, in the present invention, provided that substantial amount of heat needed for thermal fusion of synthetic resin members for medical use is provided to the heat provider through conduction heating, there will be no harm even if a certain amount of heat is generated in the heat provider itself. Further, in this specification, although the heat provider is explained taking a melting die for synthetic resin as an example, the heat provider adopted in the present invention will not be limited to the melting die for synthetic resin and further will not be limited to any type of melting die provided that synthetic resin members for medical use to be thermally fused can be mounted onto the heater unit in a connected state and be heated through heat conduction from a separate heat-generating member thus allowing the thermal fusion of the aforementioned synthetic resin members for medical use being in a connected state.

Moreover, in the present invention, it is also preferable from the following reason to adopt Joule heat as the heat for heating the heat conductive plate of the aforementioned heater unit. That is, a heating member in which the heat generating element is attached with an electric wire, such as a heater cartridge type heating member in which heating is performed by inserting a heater cartridge body 24, which is coupled with a plus side heater wire 22 and a minus side heater wire 23 as shown in FIG. 8, into a heater cartridge insertion hole 27, has a low degree of freedom in separating the heat generating element and the heated body due to the interference by the electric wire; in contrast, since Joule heat generating means such as high frequency induction heating (electromagnetic induction) means can indirectly heat the object to be heated which generates heat by a magnetic field generating apparatus, it is made possible to easily separate the apparatus for generating magnetic field from the object which is caused to generate Joule heat by the magnetic field thereby being heated. Thus, since the magnetic field generation apparatus in the present invention and the heater unit having the aforementioned heat conductive plate which is the object to be heated by the magnetic field generating apparatus can readily be made separable, it becomes possible to configure the thermal fusion apparatus of the present invention in a continuous production system. Thus, in the thermal fusion apparatus of the present invention, it is also preferable from the above view point to use Joule heat as the heat source for thermal fusing of synthetic resin members for medical use as in the aforementioned embodiment. However, the application of the thermal fusion apparatus of the present invention will not be limited to continuous production systems.

Hereinafter, the heater unit and each member constituting the thermal fusion apparatus having the aforementioned heater unit will be described in detail.

Heat Provider

The melting die for synthetic resin used as the heat provider is formed of a heat transmissive material and heated by heat transferred from the heat conductive plate. Therefore, the heat transmissive material constituting the melting die is preferably a metal having a high heat conductivity, such as copper, a copper alloy, and aluminum so that each portion of the melting die for synthetic resin is heated by heat transferred from the heat conductive plate, uniformly and rapidly as well as without heat loss.

In order that synthetic resin members for medical use to be thermally fused can be easily inserted into and clamped by the aforementioned melting die, the aforementioned die is preferably of a split type, for example, of a half-split shape which forms a parting plane 16 on both sides with respect to the direction of the axis of the tube to be clamped when the melting die clamps the thermoplastic tube 9 with a tubular member 19, which is harder than the thermoplastic tube 9, being fitted thereinto as shown in FIGS. 3 and 7. While the aforementioned parting plane 16 provides a space into which the tube escapes when the tubular members to be thermally fused together are inserted into and clamped by the aforementioned die, the aforementioned parting plane 16 will leave a stripe-like line on the surface of the thermally fused object. In order to solve this problem thereby making the parting plane to be a robust fusion surface, the aforementioned problem caused by the parting plane can be solved by using a melting die 17 of a shape having a tongued and grooved part formed in the fusion part as shown in FIG. 4, or by remelting the thermally fused synthetic resin members by means of the aforementioned die 17 after releasing the aforementioned thermally fused synthetic resin members from a state clamped by the aforementioned die 17 and rotating them.

The aforementioned melting die is disposed in a X-axis direction of the heat conductive plate in the number corresponding to the melting sites of the synthetic resin member, for example, two when there are tow melting sites. Further, disposing the multiple-die array, which is disposed in the aforementioned X-axis direction, in the Y-axis direction as well in multiple sets is more preferable, since that will allow the simultaneous thermal fusion of synthetic resin members in a larger number of melting dies.

The arrangement of the aforementioned melting die for synthetic resin may be, for example, such that heat conductive plates 12 and 12' oppositely facing in a horizontal direction are provided as shown in FIG. 2, with die bases 14 and 14' being disposed on the aforementioned plates 12 and 12', and the melting dies 13 and 13' for synthetic resin being on the die bases 14 and 14', respectively oppositely facing in a horizontal direction.

As shown in FIGS. 2 and 3, the aforementioned melting die 13 is adapted to clamp the thermoplastic tube 9 constituting an AVF needle and being connected with a thermoplastic needle base (hub) 7 which is harder than the aforementioned thermoplastic tube and forming the rear end part of a winged needle, by inserting and fitting the thermoplastic needle base into the thermoplastic tube; and the melting die 13' for synthetic resin disposed on the aforementioned die base 14' is adapted to clamp the thermoplastic tube 9 constituting the AVF needle being connected with a connector 11 for the connection of a blood circuit, by inserting and fitting the connector into the other end of the thermoplastic resin tube 9. On this occasion, clamping is preferably performed such that only the thermal fusion portion of the synthetic resin members to be thermally fused is brought into contact with the melting die for synthetic resin thus avoiding the thermal damage of the synthetic resin member. For example, when an elastomer resin is used for the soft tube and an olefin resin for the hard component, heat applied to a portion other than thermal fusion portion will degrade that portion, thereby causing the problem that the tube becomes prone to be broken or thinned.

Die Base

Although, the aforementioned melting die 13, 13' may be directly connected to the aforementioned heat conductive plate 12, 12', it is more preferable that a die base 14, 14' is firstly connected to the heat conductive plate 12, 12' and then the melting die 13, 13' is connected to this die base. Thus, interposing a die base 14, 14' between the melting die 13, 13' and the heat conductive plate 12, 12' offers an advantage that when synthetic resin members to be thermally fused are mounted to the melting die 13, 13', it is not likely that the mounted synthetic resin members will come into contact with the heated heat conductive plate 12, 12' thereby being damaged, and it becomes possible to control the thermal fusion temperature of the synthetic resin member or cool it by providing cooling means (air, water, or oil cooling) in the die base. As with the die, the die base 14, 14' also is formed of heat conductive material, preferably copper or a copper alloy which has a high heat conductivity.

Heat Conductive Plate

The heat conductive plate, which provides the aforementioned heat provider with heat, by heat conduction, for thermally fusing synthetic resin members for medical use, is comprised of a conductor, preferably a magnetic material such as steel. Preferably, the area of one heat conductive plate of aforementioned is sufficiently large to heat a plurality of the aforementioned melting dies simultaneously, since thermal fusion of synthetic resin members for medical use can be performed simultaneously and uniformly by one heating operation. For example, in FIG. 2, there are disposed in a Y-axis direction six sets of the die pair in which two melting dies 13, 13' for synthetic resin are disposed oppositely facing in a X-axis direction, where heat conductive plates 12 having a sufficient area for simultaneously heating the aforementioned die 13 group are disposed vertically above and below the aforementioned die 13 group; also heat conductive plates 12' having an sufficient area for simultaneously heating the aforementioned die 13' group are disposed vertically above and below the aforementioned die 13' group; and four heat conductive plates are disposed in total (heat conductive plates 12 and 12' disposed above the melting dies 13 and 13' are not shown in FIG. 2). However, the number of the heat conductive plates to be used is not limited to the embodiment of four plates in total as described above, and it is also possible to dispose two heat conductive plates in total, one each above and below the melting die for synthetic resin thereby heating all of the melting dies for synthetic resin. Further, as shown in FIG. 5, it is preferable to form a cut line 18, 18' in the heat conductive plate 12, 12', since forming such cut lines allow uniform heating and rapid cooling of the aforementioned heat conductive plate.

Moreover, in the heater unit of the present invention, a component which is formed by combining and connecting the heat conductive plates and the heat providers (a die, or combination of a die and a die base) is referred to as a heater unit.

Joule Heat Generating Member of Heat Conductive Plate

An example of the heating member for causing the conductive plate of the aforementioned heater unit to generate heat and performing heating by causing the heat conductive plate to produce heat includes coils 15 and 15' which are spaced apart, preferably spaced apart in parallel relationship with the heat conductive plates 12 and 12' as shown in FIGS. 3 and 5. By applying alternating current to the aforementioned coils 15 and 15', it is possible to generate heat uniformly throughout the aforementioned heat conductive plate 12, 12'. Further, as the aforementioned coil 15, 15', one commonly used in high frequency induction heating may be used. As the alternate current for creating the magnetic field to generate Joule heat, a high frequency current of several hundreds Hz to several MHz will be adopted. As the generating member for the aforementioned power source, an electric motor generator, a vacuum tube oscillator, and semiconductor devices such as a thyristor-inverter are used. Moreover, if the area of the heat conductive plate meets a relationship of heat conductive plate≦coil, it is possible to make the heat generation more uniform throughout the heat conductive plate; however, it is preferable to configure such that the areas of the heat conductive plate and the coil are approximately same, and at least the heat provider and the die base are contained in the coil, since the heat provider can be heated minimizing waste.

Hereinafter, an example of the thermal fusion method of synthetic resin members for medical use using the heater unit and the thermal fusion apparatus of the present invention will be specifically described.

The thermal fusion apparatus, for example as shown in FIGS. 2 and 3, was used to perform thermal connection of synthetic resin members which satisfy the requirement that one of the synthetic resin members for medical use to be thermally fused is a thermoplastic medical tube, and the other of them is a synthetic resin member for medical use which is to be inserted into the aforementioned thermoplastic medical tube and is a synthetic resin member for medical use harder than the aforementioned thermoplastic medical tube; and that $d'/d \geqq 1.0$ (d: inner diameter of thermoplastic tube before mounting, d': outer diameter of the synthetic resin member which is harder than the aforementioned thermoplastic tube before mounting). Since using synthetic resin members for medical use which satisfy the aforementioned requirement allows the improvement of the heat conductivity and the adhesiveness between the tube and the connector, it is made possible to achieve the advantage that the connecting strength of the thermal fusion part is increased.

Further, it is more preferable that the aforementioned thermoplastic medical tube and the synthetic resin member for medical use to be inserted into the aforementioned thermoplastic medical tube, and the heat provider (melting dies for synthetic resin) also satisfy the following requirement:

$$D \geqq D' > d'$$

(D: outer diameter of the thermoplastic tube before mounting, d': outer diameter of the synthetic resin member which is harder than the thermoplastic tube and is to be inserted into the thermoplastic tube of outer diameter D before mounting, D': inner diameter of the heat provider when mounted.)

By using synthetic resin members which satisfy the aforementioned requirement: $D \geqq D' > d'$, it is made possible to achieve the advantage that the adhesiveness between the tube and connector is improved.

A synthetic resin member for medical use to be inserted into a thermoplastic medical tube is preferably formed of a material harder than the thermoplastic tube as described above. By adopting such configuration, it is made possible to achieve the advantage that the connection site is pressed from inside thereby increasing the connecting strength of the thermal fusion part. Examples of such combinations include the combinations of: hard polycarbonate resin and soft polyvinyl chloride resin; hard polyvinyl chloride resin and soft polyvinyl chloride resin; hard polyolefin resin and soft polyolefin resin; and polyolefin resin for the hard synthetic resin member and thermoplastic elastomeric resin for the soft synthetic resin member.

Description of Symbols

Figure 1:
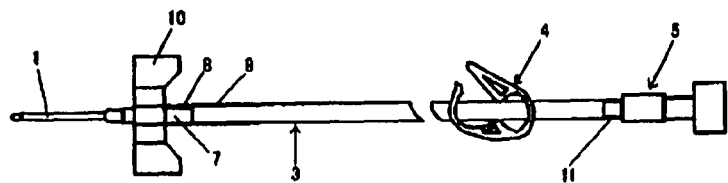
FIG. 1 is an explanatory drawing of the configuration of an AVF needle (needle 1, wing 10, and connector 5)

1 Needle
3 AVF needle
4 Clamp
5 Connector for the connection of blood circuit
7 Needle base (hub)
8 Thermal fusion part of thermoplastic tube 9 and needle base (hub) 7
9 Thermoplastic tube
10 Wing
11 Thermal fusion part of connector 5 for the connection of blood circuit and thermoplastic tube 9
12 Heat conductive plate
12' Heat conductive plate
13 Melting die for synthetic resin
13' Melting die for synthetic resin
14 Die base
14' Die base
15 Coil
15' Coil
16 Parting plane
17 Melting die for synthetic resin (tongued and grooved mold)
17' Melting die for synthetic resin (tongued and grooved mold)
18 Cut line of heat conductive plate
19 Tubular member fitted into thermoplastic tube and being harder than the tube
20 Upper melting die
21 Lower melting die
22 Plus side heater wire connected to the heater cartridge body
23 Minus side heater wire connected to the heater cartridge body
24 Heater cartridge body
25 Die base
26 Lower melting die
27 Heater cartridge body insertion hole

BEST MODE FOR CARRYING OUT THE INVENTION

Referring to the drawings, description will be made on examples of a thermal fusion apparatus used for the simultaneous thermal fusion of the needle base and the thermoplastic tube constituting an AVF needle; and the thermoplastic tube constituting the AVF needle and a connector for the connection of a blood circuit; and a fusion method for thermally fusing the components of the aforementioned AVF needle simultaneously using the aforementioned thermal fusion apparatus. Although the present examples relate to an AVF needle, the present invention can be equally applied to other thermal fusion objects such as an intravenous injection needle.

EXAMPLE 1

Figure 2:
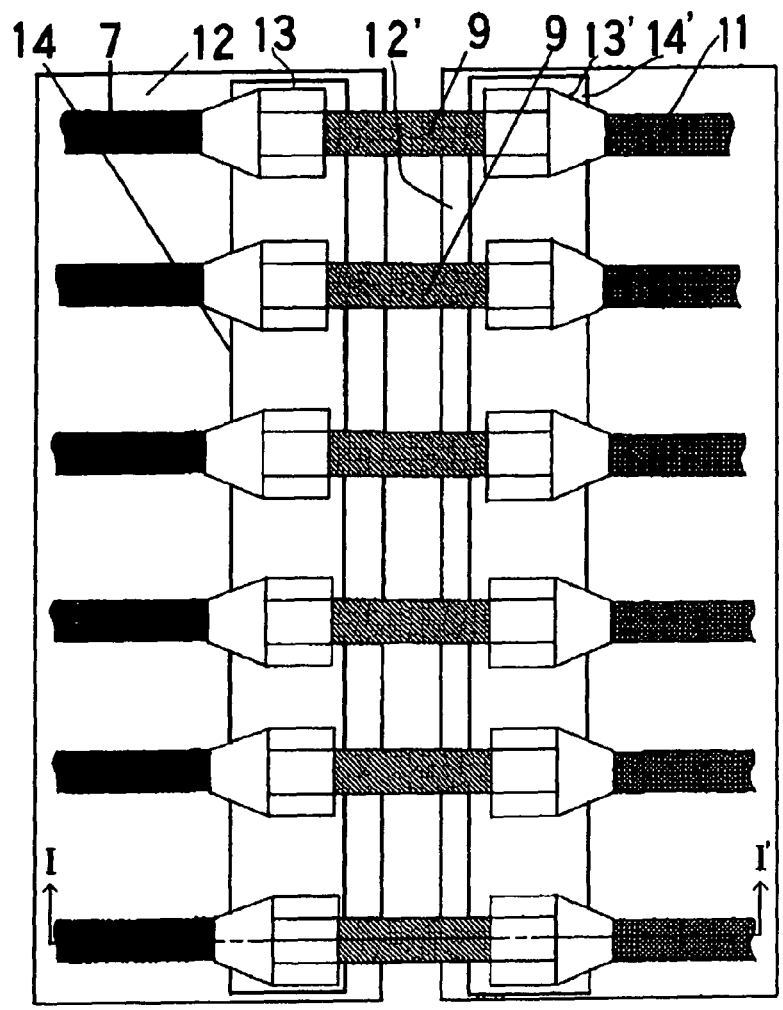
FIG. 2 is a plan view of a heater unit clamping the components of the AVF needle.

The thermal fusion apparatus for synthetic resin according to the present example is configured such that, on a pair of lower heat conductive steel plates 12 and 12' disposed oppositely facing in a horizontal direction as the heat conductive plate, there are disposed a pair of half-split dies 13 and 13' made of copper, which are melting dies for synthetic resin, oppositely facing horizontally in a X-axis direction, and six pairs in a Y-axis direction, and the heat conductive plates 12 and 12' are disposed on the upper side of the aforementioned half-split dies 13 and 13' (where, the heat conductive plates disposed on the upper side of the aforementioned half-split dies 13 and 13' are not shown in FIG. 2); and also configured to at least have: a plurality of heater units provided with each component constituting an AVF needle, i.e., a needle 1, a thermoplastic tube 9 and a connector 5 in the aforementioned half split dies 13 and 13'; heating means of the heater unit for thermally fusing each component constituting the aforementioned AVF needle; cooling means of the aforementioned heating means; and moving means for moving the aforementioned heating means of the heater unit and the heater unit heated by the heating means to the cooling means. The aforementioned die base is preferably formed with a flow path into which air, water, or other cooling media can be introduced, since the control of thermal fusion temperature or the cooling of the melting die, which is needed during thermal fusion and/or after thermal fusion by means of the heater unit shown below, can be easily performed by air or water cooling by using the aforementioned flow path. Further, an example of the aforementioned moving member may include, for example, a turning table, on which the aforementioned plurality of heater units are disposed.

Figure 3:
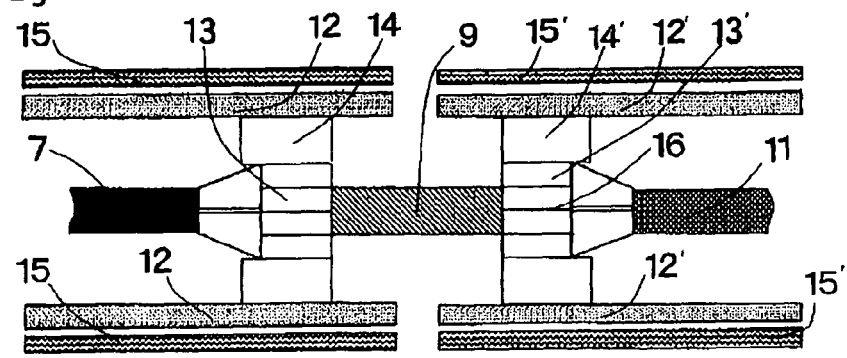
FIG. 3 is a cross sectional view taken by the I-I' line in FIG. 2.
Figure 4:
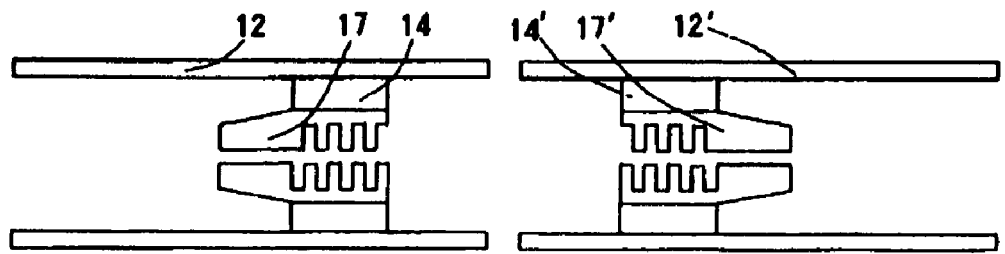
FIG. 4 is a cross sectional view of the heater unit consisting of a melting die (tongued and grooved mold), a die base, and a heat conductive plate.
Figure 5:
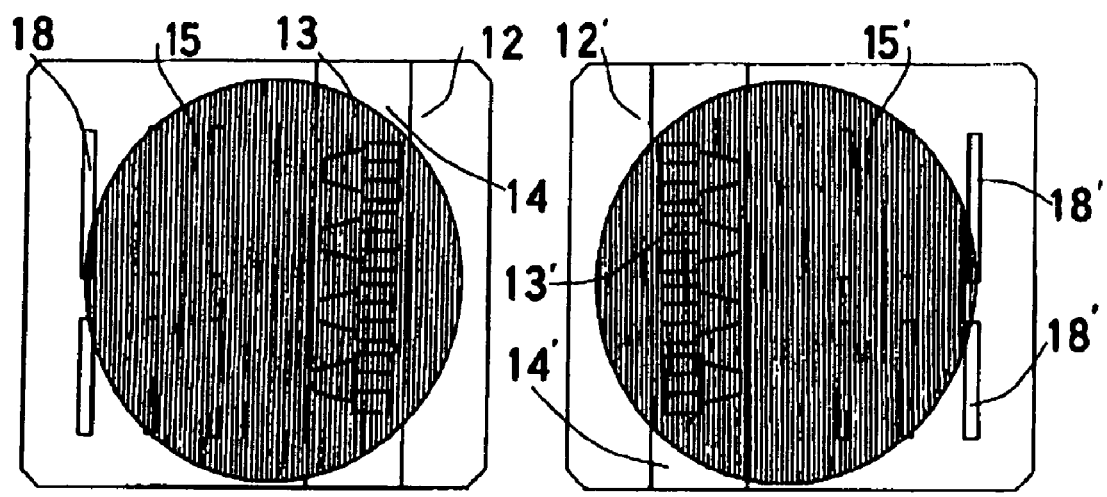
FIG. 5 is a top plan view of the heater unit disposed with the coil for the members to be thermally fused.
Figure 6:
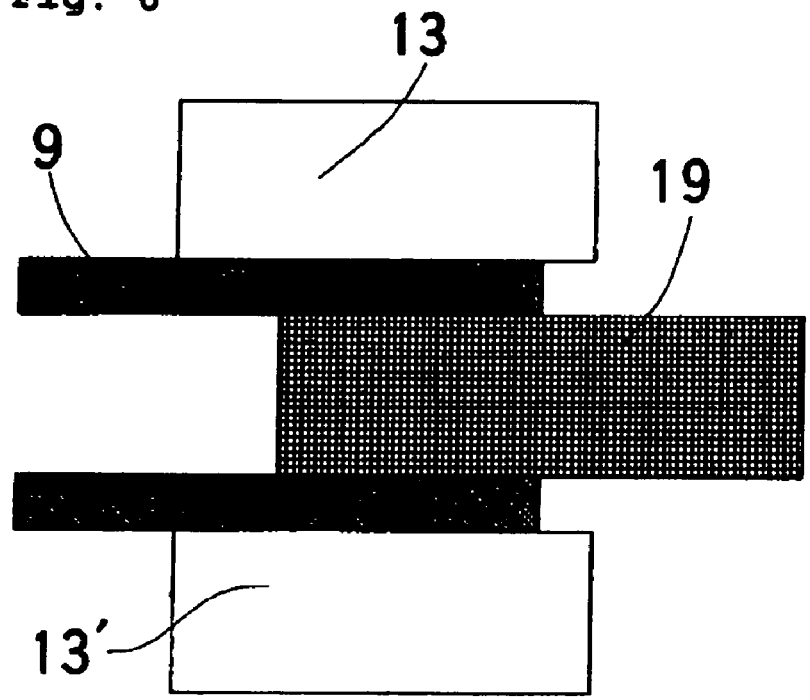
FIG. 6 is a schematic cross sectional view of the melting die (13, 13') for synthetic resin clamping the thermal fusion part of the thermoplastic tube 9 constituting the AVF needle, and the needle base (hub) 7 of a winged needle.
Figure 7:
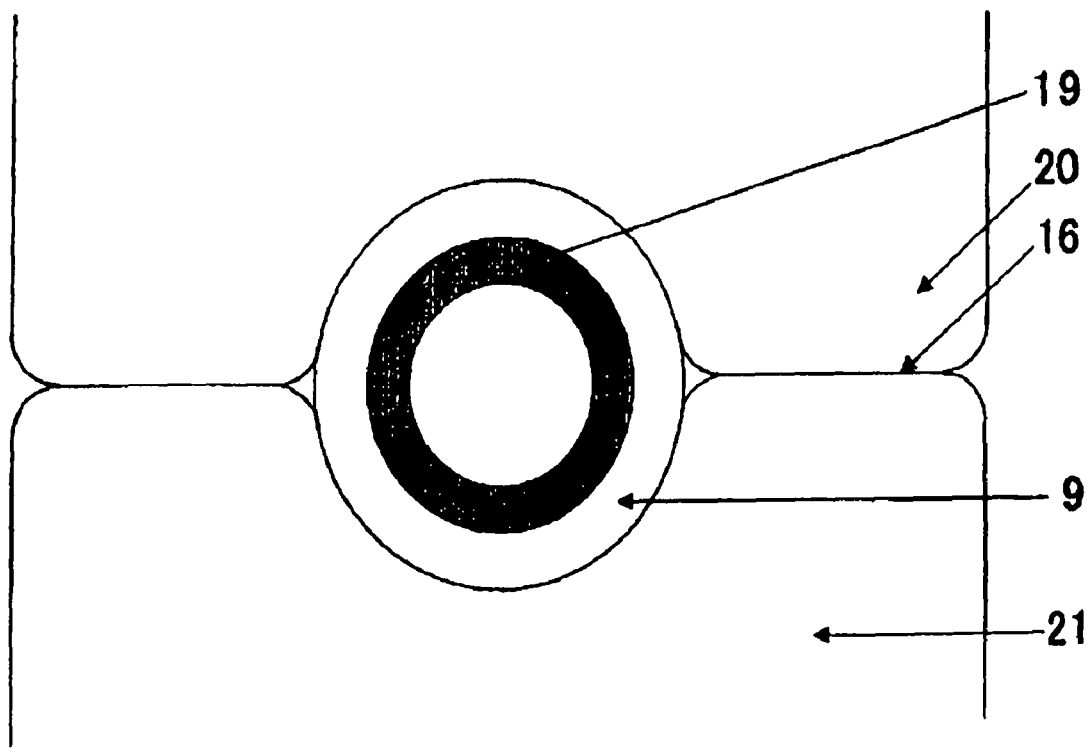
FIG. 7 is a cross sectional view to show the fitted state in the die, of the thermoplastic tube 9 clamped by the melting die for synthetic resin and an annular member 19 which is harder than the aforementioned tube and is fitted into the aforementioned tube.
Figure 8:
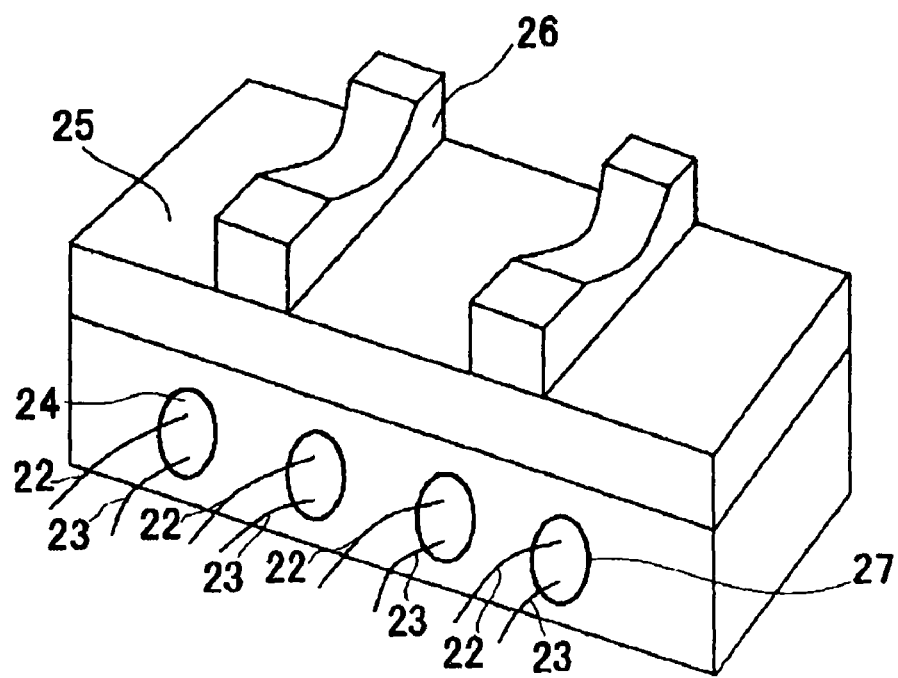
FIG. 8 a perspective view of the heater cartridge directly connected to the die and the die base.

An example of the heating means for the aforementioned heater unit includes disc type coils 15 and 15' as shown in FIG. 5, which are disposed to be able to heat the heat conductive plates 12 and 12' of the heater unit, onto which each member constituting the aforementioned AVF needle moved by the moving means is mounted, from both the upper and lower sides of them in a state being spaced apart uniformly from and in parallel with them as shown in FIGS. 2 and 3. The aforementioned heat conductive plates 12 and 12' and the disc type coils 15 and 15' preferably have substantially the same area so as to be able to heat multiple melting dies 13 and 13' for synthetic resin simultaneously and uniformly. However, the substantially same area mentioned relating to the aforementioned heat conductive plates 12 and 12' and the disc type coils 15 and 15' does not necessarily mean exactly the same area, and the aforementioned heat conductive plates 12 and 12' may have any area provided that they can heat a large number of melting dies 13 and 13' for synthetic resin simultaneously and uniformly. The aforementioned heat conductive plates 12 and 12' and the disc type coils 15 and 15' may be those which are typically used in electromagnetic cooking appliances, and the like. The aforementioned cooling means of the heater unit is the means for cooling the aforementioned heater unit which has been heated by the heating means and moved by the aforementioned moving means.

EXAMPLE 2

Thermal fusion of each member constituting the AVF needle was performed using the thermal fusion synthetic resin connecting apparatus according to the aforementioned example 1.

A plurality of aforementioned heater units are provided on a rotary table, and the thermoplastic tube (soft polyvinyl chloride resin tube) 9, which is a member constituting the AVF needle, being connected with the needle base (hub) 7 of the needle 1 made of polycarbonate resin, by inserting and fitting the needle base into the thermoplastic tube, was mounted in a clamped state onto each of the six dies 13 disposed on the melting die base 14 for synthetic resin. Similarly, the soft polyvinyl chloride resin tube 9, which is a member constituting the AVF needle, being connected with a polycarbonate resin connector for the connection of a blood circuit, by inserting and fitting the connector into the tube, was mounted in a clamped state onto each of six dies 13' disposed on the melting die base 14' for synthetic resin.

Next, one of the aforementioned plurality of heater units clamping the components of the aforementioned AVF needle in a connected state was first moved to the aforementioned heater-unit heating part by rotating the aforementioned rotary member. This heater-unit heating part had coils 15 and 15' and caused the aforementioned heat conductive plates 12 and 12' to generate Joule heat by applying a high frequency current to the aforementioned coils, and heat is transferred to the aforementioned melting dies 13 and 13' for synthetic resin to heat the melting dies 13 and 13' for synthetic resin, thereby thermally fusing the components of the aforementioned AVF needle clamped in a connected state in the aforementioned melting dies 13 and 13'. Since a half-split die is used as the melting die 13, 13', it is preferable, after the completion of the aforementioned thermal fusion, to perform thermal fusion again after closing the melting die for synthetic resin once again after releasing the melting die for synthetic resin and rotating only the synthetic resin member in order to prevent the formation of an inadequately fused part in the circumferential direction due to the lack of heating at the parting plane portion of the aforementioned melting dies for synthetic resin.

It is controlled by a control device such that when the heater unit, in which the components of the aforementioned AVF needle have been thermally fused by the aforementioned heater-unit heating portion, is moved to the aforementioned cooling means and cooled by rotating the aforementioned rotary member, simultaneously the heater unit, which clamps next components of the aforementioned AVF needle in a connected state, is moved to the aforementioned heater-unit heating part concurrently starting heating.

INDUSTRIAL APPLICABILITY

According to the present invention, a production method and a production apparatus of synthetic resin members are provided by which, when thermally fusing synthetic resin members for medical use, for example, thermally fusing a relatively soft thermoplastic tube constituting an AVF needle and other part which is harder than the aforementioned tube, such as a needle base (hub) of a winged needle or a connector for the connection of a blood circuit, an extension tube, an infusion set and the like, which is harder than the aforementioned tube; the thermal fusion of the connection part between the thermoplastic tube member and the member which is harder than the thermoplastic tube member can be performed rapidly and uniformly; and further the production process thereof can be performed automatically and continuously at a high productivity.

The invention claimed is:

1. A thermal fusion apparatus for synthetic resin members, the thermal fusion apparatus comprising:
   a heater unit comprising:
      a plurality of dies configured to mount synthetic resin members to be thermally fused in a connected state and thermally fuse a connection part of said synthetic resin members, and
      a heat conductive plate capable of being heated by induction heating, said heat conductive plate being configured to transfer enough heat to said dies when heated to thermally fuse said synthetic resin members, and said heat conductive plate having one or more slits; and
   a coil for heating the heat conductive plate of said heater unit, said coil being disposed and spaced apart from said heat conductive plate of said heater unit, and wherein said coil causes the heat conductive plate to generate Joule heat by applying an electric current to the coil.

2. The thermal fusion apparatus according to claim 1, wherein the area of the heat conductive plate and the coil are configured such that the area of the heat conductive plate are less than or equal to the area of the coil.

3. The thermal fusion apparatus according to claim 1, further comprising:
   a cooling member for the heater unit after having performed thermal fusion of the synthetic resin members.

4. The thermal fusion apparatus according to claim 3, further comprising:
   a moving member for moving the heater unit, in which synthetic resin members to be thermally fused are mounted, to the means for heating the heat conductive plate and for moving the heater unit having performed thermal fusion of synthetic resin members, to the cooling member.

5. The thermal fusion apparatus according to claim 4, wherein the moving member is a rotary member in which the heater unit is disposed.

6. The thermal fusion apparatus according to claim 4, wherein a mounting of synthetic resin members on the heater unit, a thermal fusion of the synthetic resin members mounted onto the heater unit, and a cooling of the heater unit having performed thermal fusion of synthetic resin members are performed automatically and continuously, controlled by a control apparatus.

* * * * *